United States Patent [19]

McKillop

[11] Patent Number: 5,248,781
[45] Date of Patent: Sep. 28, 1993

[54] PREPARATION OF SUBSTITUTED ANILINO-NICOTINIC ACID DERIVATIVES

[75] Inventor: Alexander McKillop, Norwich, United Kingdom

[73] Assignee: The Trustees of Princeton University, Princeton, N.J.

[21] Appl. No.: 948,507

[22] Filed: Sep. 21, 1992

[51] Int. Cl.$^5$ .................. C07D 213/26; C07C 209/62
[52] U.S. Cl. ................................. 546/310; 564/161; 564/218; 564/414
[58] Field of Search ............... 546/310; 564/414, 161, 564/218

[56] References Cited

U.S. PATENT DOCUMENTS

| Re. 26,655 | 8/1969 | Sherlock et al. | 260/295.5 |
| 3,337,570 | 8/1967 | Sherlock et al. | 260/295.5 |
| 3,689,653 | 9/1972 | Sherlock et al. | 424/266 |
| 3,839,344 | 10/1974 | Sherlock | 260/295.5 R |
| 3,891,761 | 6/1975 | Sherlock | 424/266 |
| 4,205,073 | 5/1980 | Sherlock et al. | 424/266 |
| 4,831,193 | 5/1989 | Lamendola et al. | 564/417 |

FOREIGN PATENT DOCUMENTS

| 0295674 | 12/1988 | European Pat. Off. |
| 0349902 | 1/1990 | European Pat. Off. |
| 2409260 | 1/1975 | Fed. Rep. of Germany ...... 546/310 |
| 51-005386 | 2/1976 | Japan. |
| 1406594 | 9/1975 | United Kingdom. |

OTHER PUBLICATIONS

Fuhrer, *J. Org. Chem.*, 44:1133 (1979).
Hoffman et al., *Bulletin de la Societe Chimique des France*, 7:2316 (1966).
Sliwa, *Bulletin de la Societe Chimique des France*, 2:631 (1970).
Banamine ® (Flunixin meglumine) product information sheet, NADA #101-479, Schering Corporation USA, Kenilworth, N.J. (1988).

*Primary Examiner*—Marianne M. Cintins
*Assistant Examiner*—Michael B. Hydorn
*Attorney, Agent, or Firm*—Irving N. Feit; Eric J. Sheets

[57] ABSTRACT

Substituted anilino-nicotinic acid derivatives are readily prepared from the condensation of two intermediates, 2-alkyl-3-perfluoroalkyl-anilines and alkyl 2-chloronicotinates. The 2-alkyl-3-perfluoroalkyl-aniline intermediate can be prepared via a novel three step synthesis. 3-Perfluoroalkyl-anilines are reacted with an amine directing protecting group reagent to protect the amine. The protected amine is then alkylated, and finally, the directing group is removed to form the 2-alkyl-3-perfluoroalkyl-aniline intermediate. The 2-alkyl-3-perfluoroalkyl-aniline intermediate is condensed with the alkyl 2-chloronicotinate to form the anilino-nicotinic acid derivative.

20 Claims, No Drawings

PREPARATION OF SUBSTITUTED ANILINO-NICOTINIC ACID DERIVATIVES

BACKGROUND OF THE INVENTION

It is well known that substituted anilino-nicotinic acids and their salts are useful as analgesic anti-inflammatory agents. The preparation and properties of such compounds are well-known. See U.S. Pat. Nos. 3,337,570, 3,689,653 and 3,839,344 and Belgium Patent No. 679,271.

Flunixin, a substituted anilino-nicotinic acid derivative, is particularly, a potent analgesic in clinical and veterinary applications. Considering its potency and its lack of unwanted side effects, Flunixin is a more desirable analgesic than other drugs such as morphine, meperidine hydrochloride, and pentazocine. It is well established that doses of Flunixin such as 0.25 to 10 milligrams per kilogram of body weight administered parenterally (i.e. intravenously, subcutaneously or intramuscularly) result in a potent analgesic effect.

The known processes to prepare anilino-nicotinic acid derivatives typically involve condensing a 2-alkyl-3-perfluoroalkyl-aniline intermediate with a 2-chloronicotinic acid intermediate. Problems are associated with these processes, however. The processes provide low yields of product and the 2-alkyl-3-perfluoroalkyl-aniline intermediates are difficult to prepare and purify by conventional means. Furthermore, the preparations of those intermediates are generally accompanied by a variety of byproducts. For these reasons, the preparation of substituted anilino-nicotinic acid derivatives is an expensive process. Thus, it is an object of this invention to prepare the 2-alkyl-3-perfluoroalkyl-aniline intermediate by an economic synthetic route.

SUMMARY OF THE INVENTION

The present invention is directed to a process for the preparation of substituted anilino-nicotinic acid derivatives. The process involves condensing two intermediates, a 2-alkyl-3-perfluoroalkyl-aniline and a 2-chloronicotinic acid derivative, to form an anilino-nicotinic acid derivative. The preparation of the first intermediate, the 2-alkyl-3-perfluoroalkyl-aniline is accomplished by a novel three step process. The second intermediate is prepared by a known one-step process.

To prepare the first intermediate, the 3-perfluoroalkyl-aniline is reacted with an amine directing protecting group to form an N-protected 3-perfluoroalkyl-aniline compound. An alkyl group is then added at the 2-position of the N-protected 3-perfluoroalkyl-aniline compound by combining the N-protected 3-perfluoroalkyl-aniline compound with (i) a deprotonating agent and (ii) an alkylating agent, the deprotonating agent being capable of removing a proton from an aromatic ring, to form an N-protected 2-alkyl-3-perfluoroalkyl-aniline compound. The preparation of the first intermediate is completed by removing the directing protecting group from the N-protected-2-alkyl-3-perfluoroalkyl-aniline compound by contacting it with an acidic solution, to form a substituted 2-alkyl-3-perfluoroalkyl-aniline intermediate. The perfluoroalkyl group of this intermediate may be an alkyl group with one to three carbons.

In the synthesis of the first intermediate, the amine directing protecting group reagent has the general formula R(CO)X wherein the R(CO)- group preferably has the following characteristics: 1) an ability to conjugate with the lone pair of electrons on the amine nitrogen; 2) large steric bulk; 3) an ability to coordinate with the incoming deprotonating agent; and 4) no alpha hydrogens, and X is a suitable leaving group. Preferably, the R group is a tertbutyl group. The step of reacting 3-perfluoroalkyl-aniline with the amine directing protecting group reagent is preferably carried out in an aprotic organic solvent at a temperature between about 0° C. and the boiling point of the aprotic organic solvent. More preferably, the aprotic organic solvent is an ethereal solvent.

The alkylating agent is preferably selected from the group consisting of alkyl halides, dialkyl sulfates, and alkyl tosylates, and the deprotonating agent that is capable of removing a proton from the aromatic ring is an alkyl lithium. Additionally, the step of combining the N-protected 3-perfluoroalkyl-aniline compound with the deprotonating agent is carried out in an ethereal or alkane solvent. The acidic solution that is used to remove the directing group is preferably a concentrated acid solution.

The second intermediate, the alkyl 2-chloronicotinate is prepared via known synthetic routes. Specifically, 2-hydroxy-nicotinic acid is reacted with $PCl_5$ in alcohol to form the corresponding alkyl 2-chloronicotinate. The preparation of the substituted nicotinic acid derivative is finished when the two intermediates, 2-alkyl-3-perfluoroalkyl-aniline and alkyl 2-chloronicotinate, are condensed together to form a substituted anilino-nicotinic acid derivative.

DETAILED DESCRIPTION OF THE INVENTION

The present invention is directed to the discovery that substituted anilino-nicotinic acid derivatives can be prepared using a novel process to prepare a 2-alkyl-3-perfluoroalkyl-aniline intermediate. Specifically, the invention involves the process for the preparation of the 2-alkyl-3-perfluoroalkyl-aniline intermediate from alkylation of a 3-perfluoroalkyl-aniline compound. The 2-alkyl-3-perfluoroalkyl-aniline Intermediate Known 3-perfluoroalkyl-aniline compounds react with an amine directing protecting group reagent with the general formula R(CO)X to form the N-protected 3-perfluoroalkyl-aniline compound. The R(CO)- group preferably has the following characteristics: 1) an ability to conjugate with the lone pair of electrons on the amine nitrogen; 2) large steric bulk; 3) an ability to coordinate to the incoming deprotonating agent; and 4) no alpha hydrogens. The R(CO)- group directs the deprotonation of the aromatic ring at the 2 position due to the coordination of the lithium atom to the carbonyl oxygen on the R(CO)- group. The X group in the reagent R(CO)X used to form the N-protected 3-perfluoroalkyl-aniline compound can be any of a variety of suitable leaving groups. Preferably, the X group is selected from the group consisting of halides, —O(CO)R', —N(CO)R', and —OR' where R' is an alkyl or aryl group, and the R group is a t-butyl group. More preferably, the amine directing protecting group reagent is pivaloyl chloride.

The step of reacting the 3-perfluoroalkyl-aniline with the amine directing protecting group reagent is carried out in an aprotic organic solvent at a temperature above about 0° C., but not higher than the boiling point of the aprotic organic solvent. Preferably, the aprotic organic solvent is a solution of an ethereal solvent, preferably diethyl ether or tetrahydrofuran. An acid scavenger is used if the reaction produces acid, trialkyl amine being preferred.

The N-protected 3-perfluoroalkyl-aniline compound reacts sequentially with a deprotonating agent that is capable of removing a proton from the aromatic ring to form a substituted aniline carbanion in situ, followed by quenching with an alkylating reagent to form the N-protected 2-alkyl-3-perfluoroalkyl-aniline intermediate.

The deprotonating agent can be any one of a variety of alkyl or aryl lithiums. Preferably, the deprotonating agent is a butyl lithium, more preferably n-butyl lithium.

The alkylating agent can be any one of a variety of alkylating agents that will alkylate the 2-position on the N-protected 3-perfluoroalkyl-aniline compound. The alkylating agent may be formed from a primary alkyl group with one to three carbons. Preferably, the akylating agent is selected from the group consisting of an alkyl halide, a dialkyl sulfate, and an alkyl tosylate. More preferably, the alkylating agent is methyl iodide.

The step of contacting the N-protected 3-perfluoroalkyl-aniline compound with a deprotonating agent is carried out at ambient temperature in an aprotic organic solvent which will not be deprotonated by the aromatic anion or the deprotonating agent. Preferably, the solvent is selected from the group consisting of liquid alkanes, ethers, polyethers, or a mixture of these solvents. More preferably, the solvent is tetrahydrofuran.

The resulting N-protected 2-alkyl-3-perfluoroalkyl-aniline compound is cleaved by contacting it with an acidic solution to form a 2-alkyl-3-perfluoroalkylaniline intermediate. Preferably, the acidic solution is a concentrated acid solution, more preferably a concentrated solution of hydrochloric or sulfuric acid, most preferably a 50% solution of concentrated hydrochloric acid in ethanol.

The Substituted Anilino-Nicotinic Acid Derivative

The process further includes the step of combining the 2-alkyl-3-perfluoroalkyl-aniline intermediate with a known compound, alkyl 2-chloronicotinate, to form the substituted anilino-nicotinic acid derivative. Preferably, the alkyl group of the alkyl 2-chloronicotinate is a methyl, ethyl or propyl group.

The step of combining the 2-alkyl-3-perfluoroalkyl-aniline intermediate with the alkyl 2-chloronicotinate is carried out at a temperature above about 150° C. in a high boiling aromatic solvent. Preferably, the high boiling aromatic solvent is xylene, mesitylene or cumene.

A reaction sequence for a specific example of a substituted anilo-nicotinic acid, Flunixin, is depicted in the following scheme. This scheme follows the experimental examples given below and the general scheme discussed above. Flunixin results from the last two steps. Based upon the yield of the sequence to make the first intermediate and the condensation to make the final product, the overall yield of Flunixin is about 54%.

Other examples of substituted anilo-nicotinic acids can be made according to this condensation scheme. These examples have analgesic activity like that reported for Flunixin according to Japanese Pat. No. 76,005,386. Studies indicating the dosage levels and routes of administration for substituted anilo-nicotinic acids are reported in UK Pat No. 1,406,594.

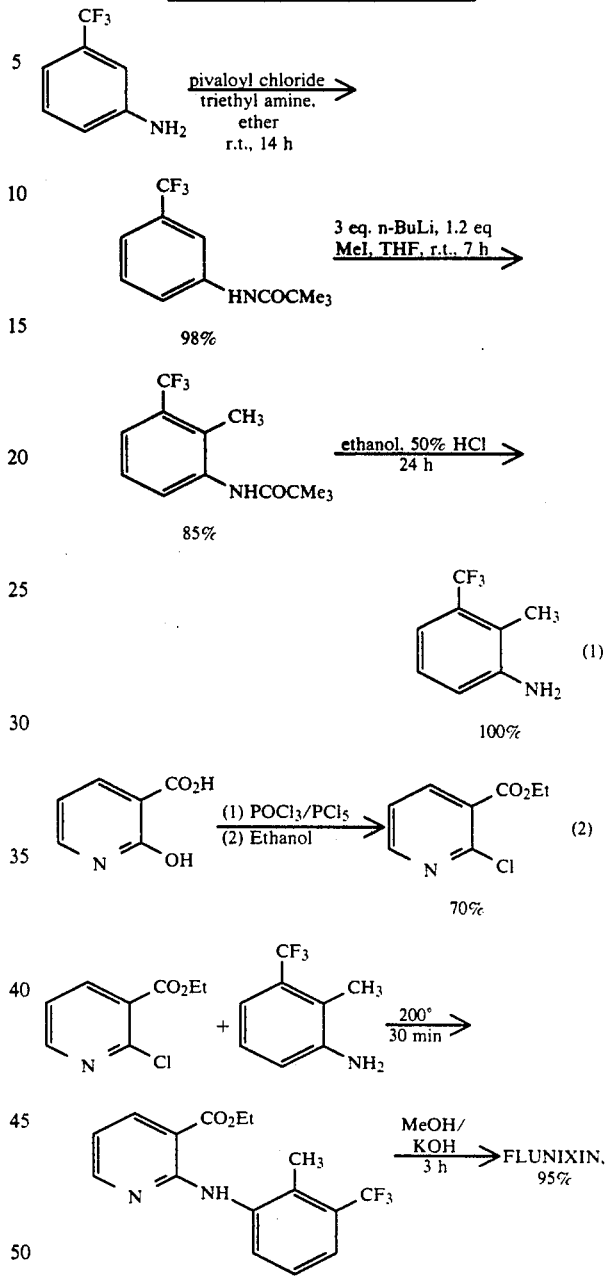

EXAMPLES

Preparation of 2,2-Dimethyl-3'-Trifluoromethyl-Propionanilide

A solution of pivaloyl chloride (3.62 g; 30 mmol) in 40 ml dry ether was added dropwise at room temperature to a mixture of 3-trifluoromethyl-aniline (4.83 g, 30 mmol) and triethylamine (4.25 ml, 30.5 mmol). This was stirred at room temperature for a period of 14 hours and then poured into 200 ml water, extracted with ether (2×100 ml). The combined ether extracts were washed successively with 0.5 HCl (100 ml); water (2×50 ml); 7% KOH (100 ml) and water (2×50 ml). The ether solution was dried with MgSO₄ and concentrated in vacuo to give a white solid (7.23 gm, 98%, m.p. 112.5° C.). The 2,2-dimethyl-3'-trifluoromethyl-propionanilide was recrystallized with dichloromethane and petroleum ether mixture.

Preparation of 2,2,2'-Trimethyl-3'-Trifluoromethyl-Propionanilide

A solution of 2,2-dimethyl-3'-trifluoromethyl-propionanilide (6.1 g, 25 mmol) in 100 ml dry tetrahydrofuran was cooled to 0° C. under nitrogen atmosphere and a solution of n-BuLi (1.6M in hexane, 50 ml, 75 mmol) was added dropwise in such a rate that the internal temperature did not rise above 10° C. (about 20 min.) and it was stirred at that temperature for 10 more minutes during which time a grayish turbidity appeared. The cooling bath was removed and the reaction mixture was stirred at room temperature for 2.5 hours. It was cooled to about 5° C. again and a solution of methyl iodide (4.258 g, 30 mmol) in tetrahydrofuran (10 ml.) was slowly transferred via a canula. It was stirred at room temperature for 4 hours and then quenched with water. The solution was concentrated in vacuo and then diluted with water and acidified with dilute HCl. It was then extracted with ether, and the ethereal extracts were washed with water followed by brine. The ether extract was dried with MgSO4 and concentrated to give a light yellow creamy solid (6.2 g., 95%). This was purified by crystallization from dichloromethane and petroleum ether mixture to afford colorless needles of 2,2,2'-trimethyl-3'-trifluoromethyl-propionanilide (80–85%, m.p. 122.5° C.).

Preparation of 2-Methyl-3-Trifluoromethyl-Aniline

A solution of 2,2,2'-trimethyl-3'-trifluoromethyl-propionanilide (10 g.) in 75 ml. ethanol and 75 ml. concentrated HCl was refluxed for 24 hours. The reaction mixture was then concentrated in vacuo and diluted with water. It was then basified with 10% NaOH solution and extracted with ether. The ether extract was washed with water and brine and dried with MgSO4. Removal of ether gave a pale brown liquid (6.65 g., 98.5%) which was purified by distillation under reduced pressure (b.p. 108°–110° C., 30 mm.) to give 5.73 g. of 2-methyl-3-trifluoromethyl-aniline which solidified on standing. The physical and spectroscopic properties of the product were found to be identical to those of an authentic sample of 2-methyl-3-trifluoromethyl-aniline prepared by the known method below.

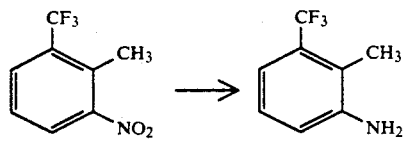

Preparation of Ethyl 2-Chloronicotinate

To a mixture of 2-hydroxynicotinic acid (13.91 g., 0.1 mole) and phosphorus pentachloride (42 g., 0.2 mole) was added phosphorus oxychloride (25 ml., excess) and then stirred at room temperature for 30 minutes. This was then heated at 120° C. for 2 hours. The reaction mixture was then concentrated in vacuo until a red viscous mass was obtained. The latter was cooled in an ice water bath and 45 ml. absolute ethanol was added first slowly and then rapidly. It was then refluxed for 30 min. and cooled. Most of the excess ethanol was removed under vacuo and the remaining mass was diluted with water (90 ml.). The aqueous solution was neutralized with 10% sodium carbonate solution and then extracted with 2×100 ml. portions of dichloromethane. The organic layer was washed with 2N NaOH solution followed by water and brine. It was dried and then concentrated to give a pale yellow liquid which was purified by distillation under reduced pressure (20 mm. Hg, b.p. 140°–44° C.) to give ethyl 2-chloronicotinate in 60–65% yield. A fore-run at 80°–110° C. (5–10%) was discarded which consisted mainly of ethyl 2-ethoxynicotinate.

The corresponding isopropyl ester was prepared in an analogous manner in 60–65% yield. However, the formation of some 2-isopropyloxy derivative could not be avoided.

Condensation of 2-Methyl-3-Trifluoromethyl-Aniline & Ethyl 2-Chloronicotinate 2-Methyl-3-trifluoromethyl-aniline (2.0 g.) was heated at 210° C. and to it was added ethyl 2-chloronicotinate (1.1 g.) dropwise. White solid was seen to sublime at the cooler region of the flask. The mixture was further heated at that temperature for 45 min. It was then cooled and water was added. The resulting mixture was extracted with ether and washed with water and brine. The ether solution was then dried and concentrated to give a dark viscous liquid. This was purified by chromatography over silica-gel and using a mixture of ether and petroleum ether (40°–60° C.) (1:2) as eluent to give 1.2 g. (62%) of ethyl 2-(2-methyl-3-trifluoromethyl-anilino)-nicotinate as a highly viscous liquid which solidified on standing. M.p. 52° C.

The ethyl 2-(2-methyl-3-trifluoromethyl-anilino)-nicotinate can be prepared alternatively by running the condensation reaction in xylene. A solution of 2-methyl-3-trifluoromethyl-aniline (2.0 g.) in 3ml of xylene was heated to boiling (bath temperature 165°–170° C.), and to it was added ethyl 2-chloronicotinate (1.1 g.) dropwise. The mixture was further heated at that temperature for 45 min. It was then cooled, dried and concentrated to give a dark viscous liquid. This was purified by chromatography over silica-gel and using a mixture of ether and petroleum ether (40°–60° C.) (1:2) as eluent to give 0.84 g. (48%) of ethyl 2-(2-methyl-3-trifluoromethyl-anilino)-nicotinate as a highly viscous liquid which solidified on standing. M.p. 52° C.

Hydrolysis to Flunixin

To a solution of ethyl 2-(2-methyl-3-trifluoromethyl-anilino) nicotinate (1.0 g.) in 15 ml. methanol was added a solution of 0.88 g. of KOH in 2 ml. water and the mixture was refluxed for four hours. It was then concentrated under vacuo diluted with water and acidified with dilute HCl. The precipitated solid was filtered, dried at 80° C. under vacuo for four hours and then recrystallized from acetone/petroleum ether to give colorless crystalline Flunixin (0.82 g., 90%). M.p. 227°–9° C.

What is claimed is:

1. A process for the preparation of a 2-alkyl-3-perfluoroalkyl-aniline intermediate, comprising:
    a) contacting a 3-perfluoroalkyl-aniline with an amine directing protecting group reagent to form an N-protected 3-perfluoroalkyl-aniline compound;
    b) combining the N-protected 3-perfluoroalkyl-aniline compound sequentially with (i) a deprotonating agent and (ii) an alkylating agent to form an N-protected 2-alkyl-3-perfluoroalkyl-aniline compound, the deprotonating agent being capable of removing a proton from an aromatic ring; and c) cleaving the N-protected 2-alkyl-3-perfluoroalkyl-aniline compound by contacting it with an acidic solution to form the 2-alkyl-3-perfluoroalkyl-aniline intermediate.

2. A process according to claim 1, further comprising the step of combining the 2-alkyl-3-perfluoroalkyl-aniline intermediate with an alkyl 2-chloronicotinate to form a substituted anilino-nicotinic acid derivative.

3. A process according to claim 1 wherein the perfluoroalkyl group is a primary alkyl group with one to three carbons.

4. A process according to claim 1 wherein the amine directing protecting group reagent has the general formula of R(CO)X wherein the R(CO)- group has an ability to conjugate with the lone pair of electrons on the amine nitrogen, is sterically hindered, is able to coordinate to incoming deprotonating agent, and contains no alpha hydrogens; and X is selected from the group consisting of halides, —O(CO)R', —N(CO)R', and —OR' wherein R, is an alkyl or aryl group.

5. A process according to claim 4 wherein the amine directing protecting group reagent is pivaloyl chloride.

6. A process according to claim 1 wherein the step of contacting 3-perfluoroalkyl-aniline with the amine directing protecting group reagent is carried out in an aprotic organic solvent.

7. A process according to claim 6 wherein the aprotic organic solvent is an ethereal solvent.

8. A process according to claim 7 wherein the aprotic organic solvent is diethyl ether.

9. The process according to claim 1 wherein the step of contacting 3-perfluoroalkyl-aniline with an amine directing protecting group is carried out at a temperature above about 0° C. and below the boiling point of the aprotic organic solvent.

10. A process according to claim 1 wherein the alkylating agent is selected from the group consisting of an alkyl halide, a dialkyl sulfate, and an alkyl tosylate wherein the alkyl group is a primary alkyl group with one to three carbons.

11. A process according to claim 10 wherein the alkylating agent is methyl iodide.

12. A process according to claim 1 wherein the deprotonating agent is an alkyl or aryl lithium.

13. A process according to claim 12 wherein the deprotonating agent is n-butyl lithium.

14. A process according to claim 1 wherein the step of combining the N-protected 3-perfluoroalkyl-aniline intermediate sequentially, with (i) a deprotonating agent and (ii) an alkylating agent is carried out in an solvent selected from the group consisting of a liquid alkane, an ether, a polyether, and a mixture thereof.

15. A process according to claim 14 wherein the solvent is tetrahydrofuran.

16. A process according to claim 1 wherein the acidic solution is a concentrated hydrochloric or sulfuric acid solution.

17. A process according to claim 16 wherein the acidic solution is about a 50% solution of concentrated hydrochloric acid in ethanol.

18. A process according to claim 2 wherein the alkyl group of the alkyl 2-chloronicotinate is methyl, ethyl, or propyl.

19. A process according to claim 2 wherein the step of combining the 2-alkyl-3-perfluoroalkyl-aniline intermediate with ethyl 2-chloronicotinate is carried out in a high boiling aromatic solvent.

20. A process according to claim 19 wherein the high boiling aromatic solvent is xylene, mesitylene or cumene.

* * * * *

UNITED STATES PATENT AND TRADEMARK OFFICE
CERTIFICATE OF CORRECTION

PATENT NO. : 5,248,781
DATED : September 28, 1993
INVENTOR(S) : McKillop

It is certified that error appears in the above-indentified patent and that said Letters Patent is hereby corrected as shown below:

The title page, should be deleted to be replaced with attached title page.

Signed and Sealed this

Twenty-sixth Day of July, 1994

Attest:

BRUCE LEHMAN

*Attesting Officer*     *Commissioner of Patents and Trademarks*

United States Patent [19]

McKillop

[11] Patent Number: 5,248,781
[45] Date of Patent: Sep. 28, 1993

[54] PREPARATION OF SUBSTITUTED ANILINO-NICOTINIC ACID DERIVATIVES

[75] Inventor: Alexander McKillop, Norwick, United Kingdom

[73] Assignee: MacLeod Pharmaceuticals Inc., Fort Collins, Co.

[21] Appl. No.: 948,507

[22] Filed: Sep. 21, 1992

[51] Int. Cl.$^5$ .................... C07D 213/26; C07C 209/62
[52] U.S. Cl. ...................................... 546/310; 564/161; 564/218; 564/414
[58] Field of Search ................. 546/310; 564/414, 161, 564/218

[56] References Cited

U.S. PATENT DOCUMENTS

| | | | |
|---|---|---|---|
| Re. 26,655 | 8/1969 | Sherlock et al. | 260/295.5 |
| 3,337,570 | 8/1967 | Sherlock et al. | 260/295.5 |
| 3,689,653 | 9/1972 | Sherlock et al. | 424/266 |
| 3,839,344 | 10/1974 | Sherlock | 260/295.5 R |
| 3,891,761 | 6/1975 | Sherlock | 424/266 |
| 4,205,073 | 5/1980 | Sherlock et al. | 424/266 |
| 4,831,193 | 5/1989 | Lamendola et al. | 564/417 |

FOREIGN PATENT DOCUMENTS

| | | |
|---|---|---|
| 0295674 | 12/1988 | European Pat. Off. |
| 0349902 | 1/1990 | European Pat. Off. |
| 2409260 | 1/1975 | Fed. Rep. of Germany ........ 546/310 |
| 51-005386 | 2/1976 | Japan . |
| 1406594 | 9/1975 | United Kingdom . |

OTHER PUBLICATIONS

Fuhrer, *J. Org. Chem.*, 44:1133 (1979).
Hoffman et al., *Bulletin de la Societe Chimique des France*, 7:2316 (1966).
Sliwa, *Bulletin de la Societe Chimique des France*, 2:631 (1970).
Banamine ® (Flunixin meglumine) product information sheet, NADA #101-479, Schering Corporation USA, Kenilworth, N.J. (1988).

*Primary Examiner*—Marianne M. Cintins
*Assistant Examiner*—Michael B. Hydorn
*Attorney, Agent, or Firm*—Irving N. Feit; Eric J. Sheets

[57] ABSTRACT

Substituted anilino-nicotinic acid derivatives are readily prepared from the condensation of two intermediates, 2-alkyl-3-perfluoroalkyl-anilines and alkyl 2-chloronicotinates. The 2-alkyl-3-perfluoroalkyl-aniline intermediate can be prepared via a novel three step synthesis. 3-Perfluoroalkyl-anilines are reacted with an amine directing protecting group reagent to protect the amine. The protected amine is then alkylated, and finally, the directing group is removed to form the 2-alkyl-3-perfluoroalkyl-aniline intermediate. The 2-alkyl-3-perfluoroalkyl-aniline intermediate is condensed with the alkyl 2-chloronicotinate to form the anilino-nicotinic acid derivative.

20 Claims, No Sheets